(12) United States Patent
Munsinger (10) Patent No.: US 6,228,110 B1
(45) Date of Patent: May 8, 2001

(54) STENT DELIVERY SYSTEM (75) Inventor: Joel R. Munsinger, Albertville, MN (US)

(73) Assignee: SciMed Life Systems, Inc., Maple Grove, MN (US)

(*) Notice: Subject to any disclaimer, the term of this patent is extended or adjusted under 35 U.S.C. 154(b) by 0 days.

(21) Appl. No.: 09/472,618

(22) Filed: Dec. 27, 1999

Related U.S. Application Data (62) Division of application No. 09/105,321, filed on Jun. 26, 1998, now Pat. No. 6,117,140.

(51) Int. Cl.[7] ................. A61F 11/00; A61F 2/06
(52) U.S. Cl. .............. 623/1.12; 623/1.11; 606/194; 606/108; 604/96.01
(58) Field of Search .................. 606/108, 194, 606/191, 195, 198; 604/96.01; 623/1.11, 1.12

(56) References Cited

U.S. PATENT DOCUMENTS

| | | | |
|---|---|---|---|
| 4,932,959 | * | 6/1990 | Horzewski et al. ............... 606/194 |
| 4,936,310 | * | 6/1990 | Engstrom et al. ................. 600/486 |
| 5,003,990 | | 4/1991 | Osypka . |
| 5,045,061 | * | 9/1991 | Seifer et al. ....................... 604/96 |
| 5,085,636 | * | 2/1992 | Burns ................................ 604/99 |
| 5,141,494 | | 8/1992 | Danforth et al. .................. 604/96 |
| 5,443,457 | * | 8/1995 | Ginn et al. ........................ 604/280 |
| 5,788,707 | | 8/1998 | Del Toro et al. ................. 606/108 |
| 5,810,867 | | 9/1998 | Zarbatany et al. ............... 606/191 |
| 5,980,533 | | 11/1999 | Holman . |

FOREIGN PATENT DOCUMENTS

| | | |
|---|---|---|
| 0 371 486 A1 | 6/1990 | (EP) . |
| 0 745 409 A1 | 12/1996 | (EP) . |
| 0 819 413 A2 | 1/1998 | (EP) . |
| 97/48343 | 12/1997 | (WO) . |
| 99/59664 | 11/1999 | (WO) . |

* cited by examiner

Primary Examiner—Michael H. Thaler
Assistant Examiner—Vy Q. Bul
(74) Attorney, Agent, or Firm—Vidas, Arrett & Steink

(57) ABSTRACT

Inventive catheters are disclosed which employ a variety of devices for preventing unwanted motion of the catheter tip. These methods include the use of a slidably mounted annular shim located in the tip of the catheter which may frictionally engage the guidewire element, and an annular brush with bristles. In the later case, the extent of the frictional engagement between the tip and the guidewire is determined by the orientation of the bristles. The present invention is also directed to a catheter in which unwanted motion is prevented by the presence of a tension/compression cable extending from the proximal end of the catheter shaft to the distal end of the catheter shaft. In the unlocked position, the tension/compression cable has slack in it while in the engaged position, the cable is either under tension or under compression.

12 Claims, 7 Drawing Sheets

STENT DELIVERY SYSTEM

CROSS REFERENCE TO RELATED APPLICATIONS

This application is a Divisional application from U.S. application Ser. No. 09/105,321, filed Jun. 26, 1998, now U.S. Pat. No. 6,117,140 the contents of which is hereby incorporated by reference

BACKGROUND OF THE INVENTION

In the treatment of diseases of the cardiovascular system, a variety of treatment devices are delivered by a catheter to a desired location in a bodily vessel. These treatment devices include balloons, stents and optical fibers carrying laser light.

In typical PTCA procedures, a guiding catheter is percutaneously introduced into the cardiovascular system of a patient and advanced through the aorta until the distal end is in the ostium of the desired coronary artery. Using fluoroscopy, a guide wire is then advanced through the guiding catheter and across the site to be treated in the coronary artery. An over the wire (OTW) balloon catheter is advanced over the guide wire to the treatment site. The balloon is then expanded to reopen the artery. The OTW catheter may have a guide wire lumen which is as long as the catheter or it may be a rapid exchange catheter wherein the guide wire lumen is substantially shorter than the catheter. Alternatively, a fixed wire balloon may be used. This device features a guide wire which is affixed to the catheter and cannot be removed.

To help prevent arterial closure, repair dissection, or prevent restenosis, a physician can implant an intravascular prosthesis, or a stent, for maintaining vascular patency inside the artery at the lesion. The stent may either be a self-expanding stent or a balloon expandable stent. For the latter type, the stent is often delivered on a balloon and the balloon is used to expand the stent. The self-expanding stents may be made of shape memory materials such as nitinol or constructed of regular metals but of a design which exhibits self expansion characteristics.

Catheters are also used to deliver optical fibers carrying laser light to provide controlled delivery of a laser beam for treatment of atherosclerotic disease.

It is often desirable to provide a retractable sheath as a cover over a treatment device until the treatment device is positioned. At that point, the retractable sheath is removed and the treatment device delivered to the desired location.

Consequently, as the retractable sheath of a catheter is retracted to allow for deployment of a stent or other treatment device, the tip of the catheter has a tendency to move. In particular, where the catheter traverses a twisted, curved pathway, a portion of the catheter, including the tip, upon retraction of the sheath, will have a tendency to move either to the inside of the curve or to the outside of the curve from its position in the center of the pathway resulting in the tip moving forward. This movement of the tip can complicate the precise deployment of a stent or other treatment device as the practitioner cannot be certain of the exact location of the catheter tip as the treatment device is deployed.

In an effort to address this difficulty, the present invention is directed toward a catheter in which the movement of the tip associated with retraction of the catheter is eliminated via a locking means. Two principal approaches are used to accomplish this goal. In one approach, the guidewire is locked to the tip prior to retraction of the sheath. In the other approach, the catheter shaft exhibits a controllable variable flexibility. Motion of the tip is prevented by increasing the rigidity of the catheter prior to retraction of the sheath.

SUMMARY OF THE INVENTION

The object of the present invention is a catheter in which undesired motion may be reduced or eliminated. Such a catheter is embodied by a lockable treatment device delivery catheter comprising an inner tube, a guidewire element carried within the inner tube and extending from the proximal end of the inner tube to the distal end of the inner tube, a tip mounted over the inner tube at the distal end of the inner tube and a motion arresting device frictionally engaging the tip of the catheter with the guidewire to prevent proximal and/or distal motion of the tip when engaged.

Several specific embodiments of the motion arresting device including a shim slidably mounted within the tip and a brush mounted within the tip are disclosed. In both cases, the motion arresting device is mounted concentrically about the guidewire element. In the former case, the shim is slidably mounted so that when in use the shim slides from a region of the tip with a larger inner diameter to a region with a lower inner diameter, thereby applying an inward force to the shim which then frictionally engages the proximal region of the tip and the guide wire, fixing one to the other. In the latter case, an annular brush having bristles directed radially inward is mounted concentrically over the guidewire. As the guidewire is moved relative to the bristles, the orientation of the bristles changes (either from proximal to distal or vice versa). As the bristles reorient, the force required to continue the reorientation increases to the point where the guidewire is effectively locked to the tip.

In another embodiment, the invention provides a variably flexible catheter. The variable flexibility is achieved by the inclusion of a tension-compression cable in the catheter. The tension-compression cable is anchored at the distal end of the catheter and preferably in a retractable sheath, where present. Increased rigidity is achieved by placing the tension-compression either in tension or in compression from a relaxed state. This increased rigidity may be exploited to prevent undesired motion of the catheter tip.

The present invention is also directed to a method of delivering a treatment device such as a stent to a desired bodily location using the inventive devices.

BRIEF DESCRIPTION OF THE FIGURES

FIG. 2b show a further enlarged schematic of FIG. 2a.

DETAILED DESCRIPTION OF THE INVENTION

While this invention may be embodied in many different forms, there are described in detail herein specific preferred embodiments of the invention. This description is an exemplification of the principles of the invention and is not intended to limit the invention to the particular embodiments illustrated.

Figure 1:
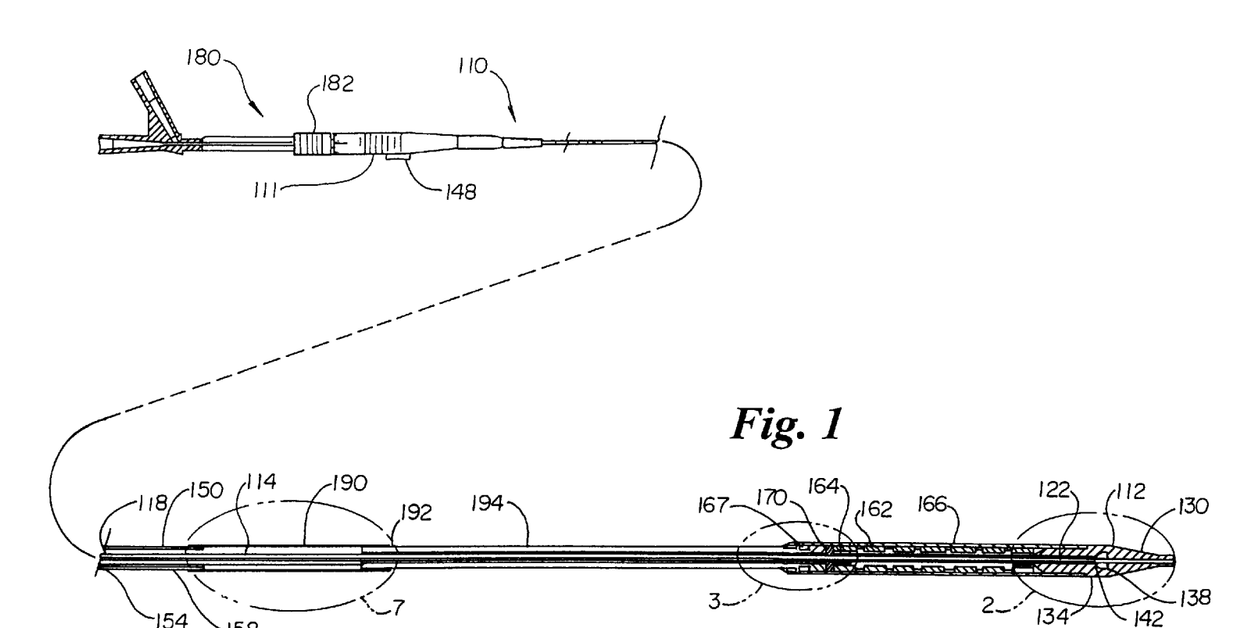
FIG. 1 show a longitudinal cross-section of an inventive catheter.
Figure 2A:
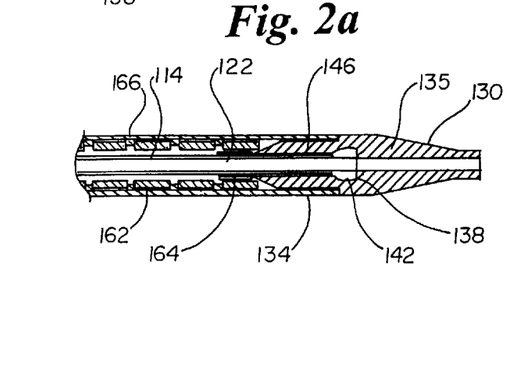
FIG. 2a shows an enlarged view of the circled region 2 of the catheter in FIG. 1.
Figure 2B:
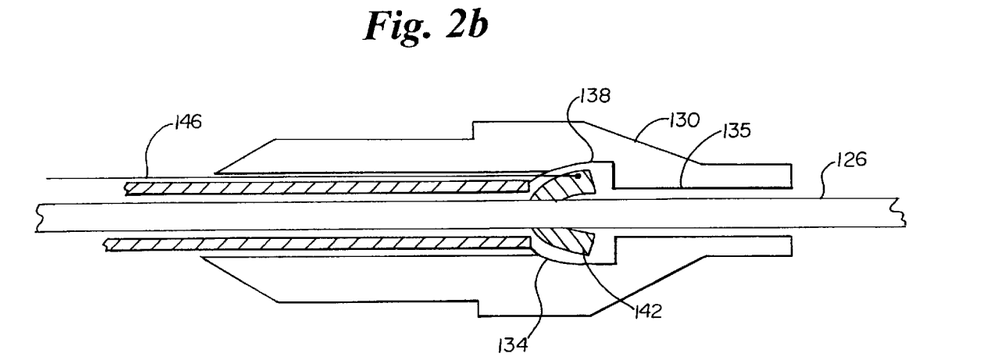
Figure 6:
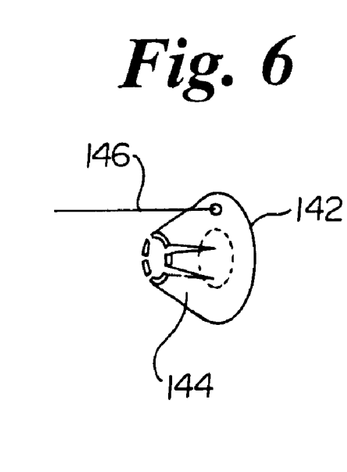
FIG. 6 shows the shim of FIG. 4 in perspective view.

FIG. 1 shows a longitudinal cross-section of an inventive catheter generally at 110 having proximal 111 and distal 112 ends. The catheter comprises an inner tube 114 having a proximal end 118 and a distal end 122. Carried within inner tube 114 is a guidewire element 126, which is shown in FIGS. 2a,b. Guidewire element 126 extends beyond distal end 122 of inner tube 114. Catheter 110 further comprises a tip 130 mounted over distal end 122 of inner tube 114. Tip 130 has a proximal region 134 and a intermediate region 138 distal to and adjacent to proximal region 134. The inner diameter of intermediate region 138 exceeds the inner diameter of proximal region 134 of tip 130 and the inner diameter of distal region 135 of the tip so as to accommodate a motion arresting device 142. Motion arresting device 142 frictionally engages tip 130 with guidewire element 126 to prevent proximal and/or distal motion of the tip when engaged. As shown in FIGS. 1, 2a,b and 4–8, motion arresting device 142 is a tapered shim 142 slidably mounted in tip 130. Shim 142 is controlled by a shim pullwire 146 attached thereto extending to a shim actuator 148 at proximal end 111 of catheter 110. Shim 142 is shown in longitudinal cross-sectional view in FIG. 4 and in transverse cross-sectional view along line 5—5 in FIG. 5. Shim 142 is further shown in perspective view in FIG. 6. As seen in the figures, shim 142 is preferably in the form of a collet with fingers 144. As seen in FIG. 1, shim 142 is not in contact with guidewire element 126 and as such, the shim is not engaged.

As shown in FIG. 1, catheter 110 further comprises an optional proximal catheter shaft 150 having a proximal end 154 and a distal end 158. Inner tube 114 is carried within proximal catheter shaft 150 and extends beyond distal end 158 of proximal catheter shaft 150. Also shown in FIG. 1 is an optional treatment delivery device, in this case a stent 162, mounted over distal end 122 of inner tube 114. Shown covering stent 162 is an optional retractable sheath 166 slidably mounted on distal catheter shaft 194. Retractable sheath 166 is retractable from a fully extended position (as shown) in which the treatment device, stent 162, is covered by the retractable sheath and a fully retracted position (not shown) in which the treatment device, stent 162, is exposed.

As seen in FIG. 1, tip 130 abuts retractable sheath 166, in the fully extended position. Retractable sheath 166 may be retracted by pulling on sheath pullwire 169 which is attached to pull collar 167 which, in turn, is attached to retractable sheath 166. Sheath pullwire 169 extends to the proximal end of the catheter.

At the proximal end of the catheter is an optional manifold structure, shown generally at 180, with slide mechanism 182 as is known in the art. Slide mechanism 182 is connected to sheath pullwire 169 in a known manner for retracting sheath 166 by moving the slide mechanism.

Also shown in FIG. 1 are marker band 164 and bumper 170 as are known in the art.

Figures 4, 5, 7:
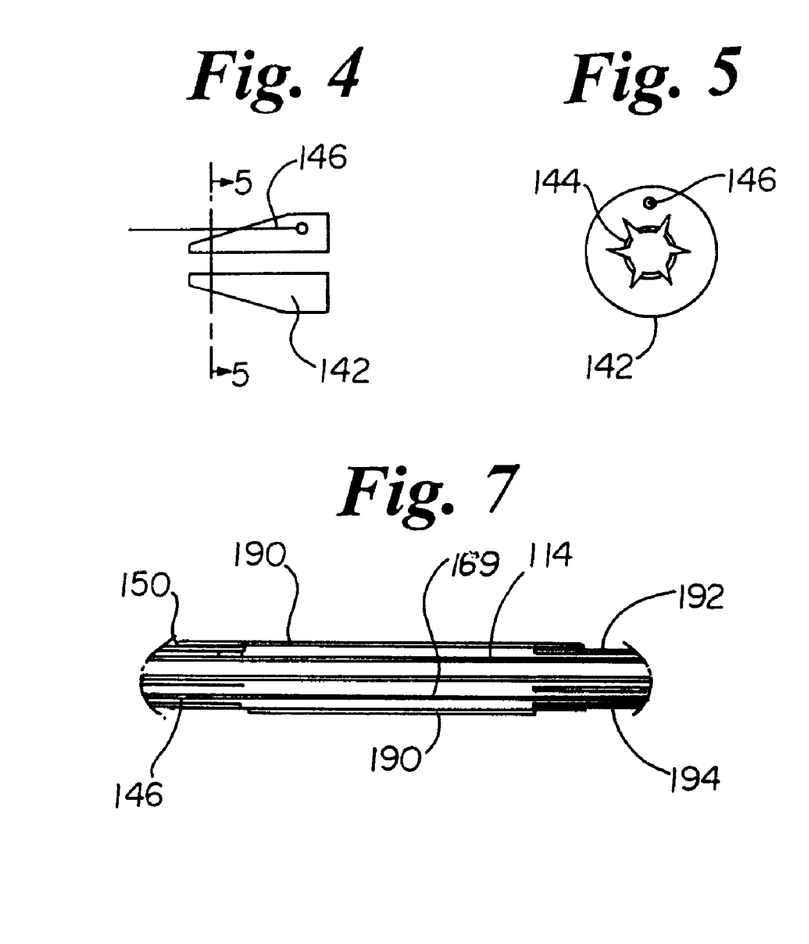
FIG. 4 shows the shim in longitudinal cross-sectional view.
FIG. 5 shows the shim of FIG. 4 in transverse cross-sectional view along line 5—5.
FIG. 7 shows an enlarged view of the circled region 7 of the catheter in FIG. 1.

In use, tip 130 is locked to guidewire element 126 by pulling shim pullwire 146 proximally thereby sliding shim 142 in a proximal direction. While shim 142 is in intermediate region 138 of tip 130, it slides freely because the inner diameter of the tip in the intermediate region exceeds the outer diameter of the shim. As shim 142 enters proximal region 134, the shim becomes wedged therein because the maximum outer diameter of the tip exceeds the inner diameter of the proximal region of the tip as shown in FIG. 5.

The shim should be flexible enough to deform inward. The shim may be made of a flexible material which can deform inward so as to engage the guidewire element. The material may be flexible. Alternatively, the shim may be made of a rigid material which is constructed and arranged to collapse inward. An example of the latter is a collet. The tip, however, must be rigid, relative to the shim. Suitable materials from which the shim may be made include olefinics, polyurethanes, polyesters, styrenics and polyamides and combinations thereof.

Shim pullwire 146 may be welded to the shim or alternatively, may be heat welded to the plastic where the shim is formed of plastic or may be adhesively bonded to the shim or otherwise connected thereto.

Guidewire element 126 may consist solely of a guidewire or may comprise a guidewire as well as a guidewire sheath or tube in which the guidewire is carried. Where the guidewire element has a protective sheath bonded or otherwise affixed to the guidewire and the sheath and guidewire slide in unison, the shim will simultaneously engage the guidewire and sheath. Where, on the other hand, the guidewire element comprises a guidewire slidably carried within the lumen of a tube, the tube must be deformable inward so that the shim may engage the guidewire through the tube.

In the embodiment of FIG. 1, as shown in FIG. 7, the catheter further comprises an accordion assembly 190 extending from the distal end 158 of proximal catheter shaft 150 to the proximal end 192 of distal catheter shaft 194.

Figure 9:
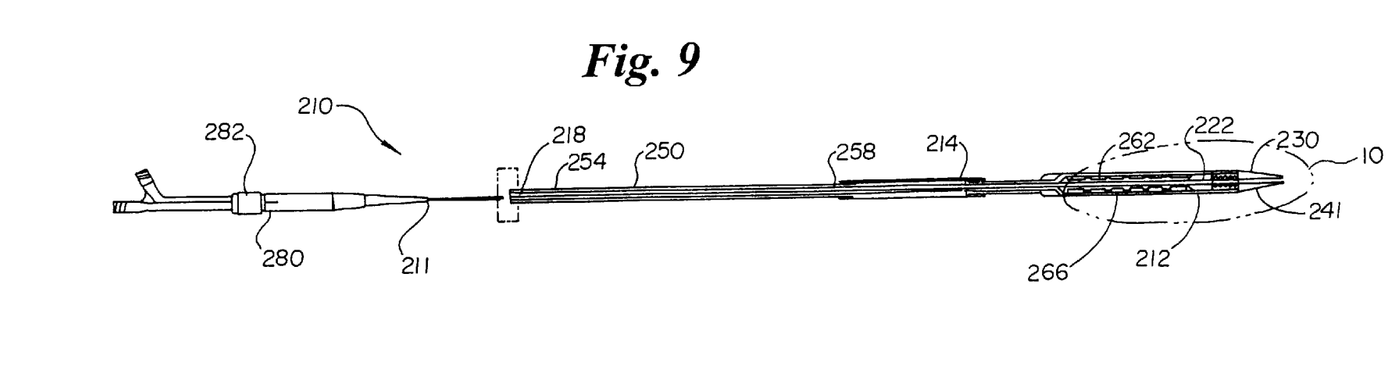
FIG. 9 shows another embodiment of the inventive catheter.
Figure 10:
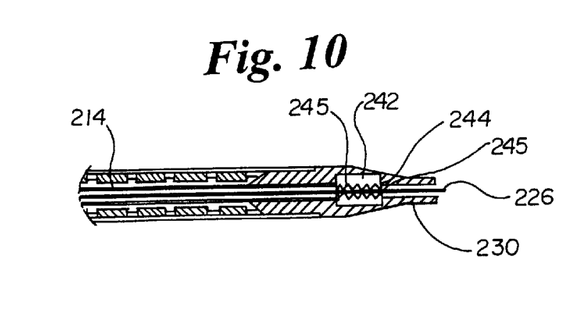
FIG. 10 shows an enlarged longitudinal cross-section view of the circled region 10 of the catheter in FIG. 9 with the brush in the unlocked position.
Figure 11:
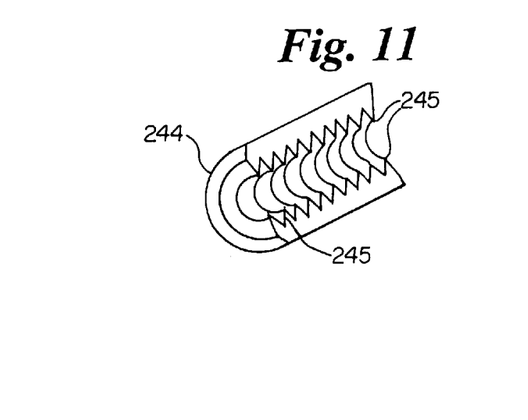
FIG. 11 shows a perspective, cross-sectional view of the brush used in the catheter of FIG. 9.

In another embodiment of the invention, as shown in FIGS. 9–12, catheter 210 having proximal 211 and distal 212 ends comprises an inner tube 214 having a proximal end 218 and a distal end 222. Carried within inner tube 214 is a guidewire element 226. Guidewire element 226 extends beyond distal end 222 of inner tube 214. Catheter 210 further comprises a tip 230 mounted over distal end 222 of inner tube 214. Catheter 210 further comprises a motion arresting device 242 frictionally engaging tip 230 with guidewire element 226 to prevent proximal and/or distal motion of the tip when engaged. As shown in FIG. 10, an expanded view of the circled region in FIG. 9, motion arresting device 242 comprises a an annular brush 244 therein, the brush having bristles 245. Annular brush 244 is mounted within tip 230 concentrically about guidewire element 226. Bristles 245 extend from brush 244 to guidewire element 226 and frictionally engage at least a portion of the guidewire element. A cross-sectional perspective view of brush 244 with bristles 245 is shown in FIG. 11.

Figure 8:
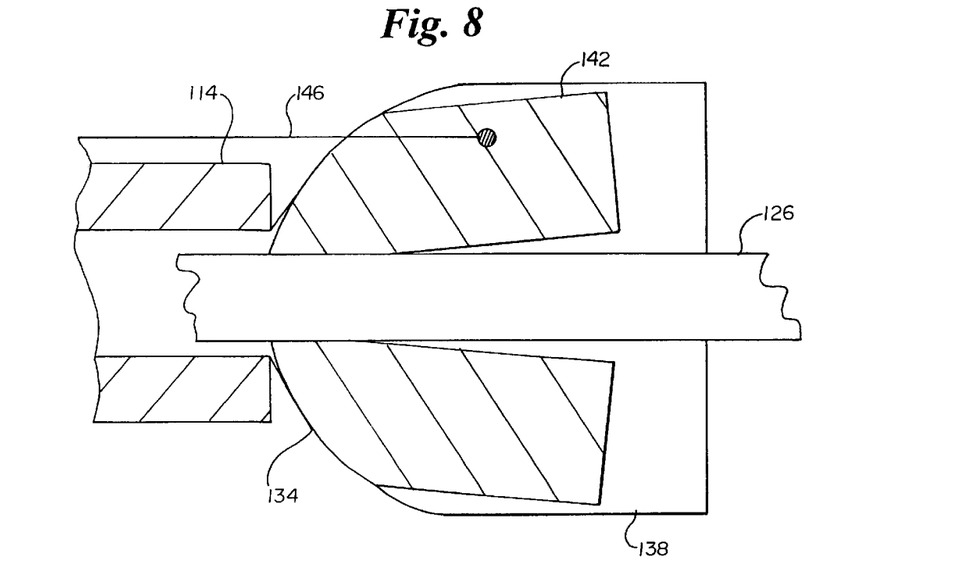
FIG. 8 is a schematic drawing of the tip of the catheter of FIG. 1 with the motion arresting device engaged.

As shown in FIG. 9, catheter 210 further comprises an optional catheter shaft 250 having a proximal end 254 and a distal end 258. Inner tube 214 is carried within catheter shaft 250 and extends beyond distal end 258 of catheter shaft 250. Also shown in FIG. 8 is an optional treatment delivery device, a stent 262, mounted over distal end 222 of inner tube 214. Shown covering stent 262 is an optional retractable sheath 266 mounted on distal end 258 of catheter shaft 250. Retractable sheath 266 is retractable from a fully extended position (as shown) in which the treatment device, stent 262, is covered by the retractable sheath and a fully retracted position in which the treatment device, stent 262, is exposed. As seen in FIG. 9, tip 230 abuts retractable sheath 266, in the fully extended position.

Figure 3:
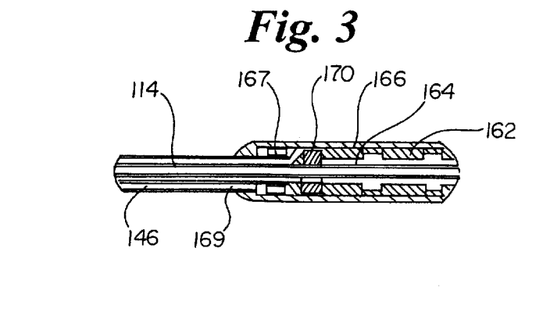
FIG. 3 shows an enlarged view of the circled region 3 of the catheter in FIG. 1.

At the proximal end of the catheter is a manifold structure 280 with slide mechanism 282 as is known in the art. Slide mechanism 282 is connected to a pull wire (not shown) similar to sheath pullwire 169 shown in FIG. 3 in a known manner for retracting sheath 266 by moving the slide proximally.

Figure 12:
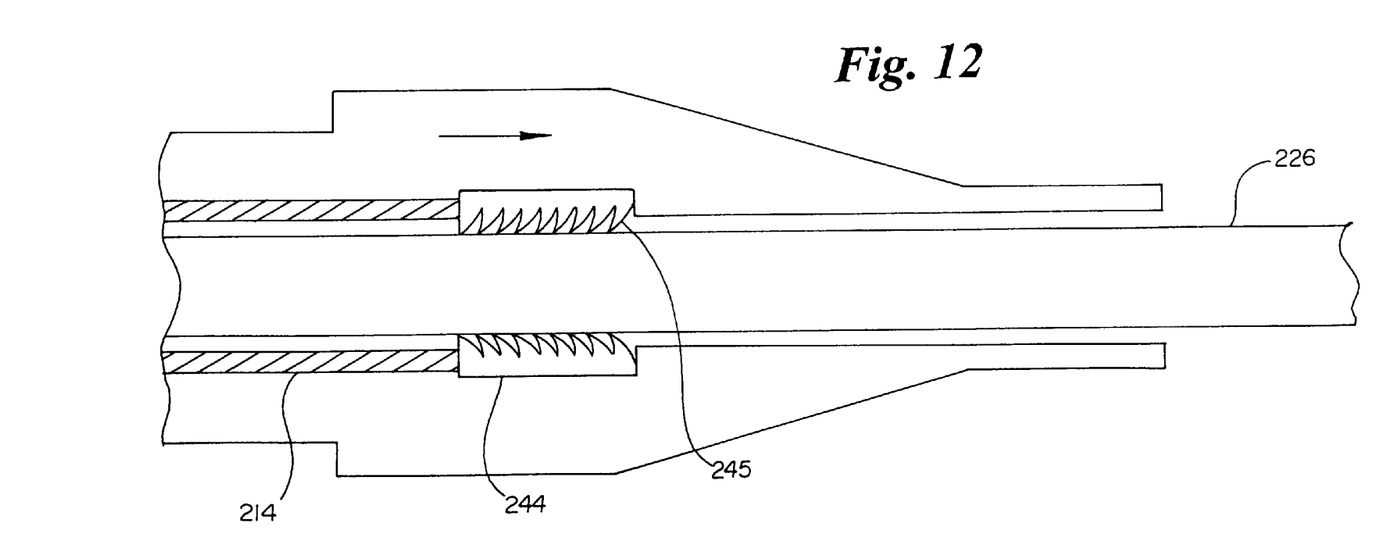
FIG. 12 shows a schematic cross-sectional view of the tip of the catheter of FIG. 9 with the bristles of the brush in the locked position.

In order to more fully understand the operation of the motion arresting device, brush 244 is shown in a perspective cut-away view in FIG. 11. Bristles 245 are more clearly seen to extend from the brush inward. A schematic drawing of tip 230 is shown in FIG. 12 in which bristles 245, engaging guidewire element 226 are shown oriented in the proximal direction. As long as guidewire 226 is moved in a proximal direction relative to the rest of the catheter, guidewire element 226 will meet a fixed resistance from the brush. When it is desired to lock guidewire element 226 in place, the motion of guidewire element 226 is reversed relative to the catheter at which point bristles 245 begin to reorient, as shown in FIG. 10 thereby resulting in an increased resistance to motion resulting from the interaction of the bristles with the guidewire element thereby locking the guidewire to the tip. Note that FIG. 10 does not represent a locked position, but rather an intermediate position. Of course, if enough force is applied to the guidewire element, the guidewire and tip may be unlocked with the orientation of the bristles reversing entirely so as to be facing in the distal direction at which point, the guidewire element will face a constant, but reduced resistance to distal motion, thereby disengaging the tip from the guidewire element. The guidewire element may again be locked by again reversing the direction of motion of the guidewire element so as to partially reorient the bristles. In a more general way, when the bristles are oriented proximally, the guidewire may be moved with little resistance in the proximal direction but will be more resistant to motion in the distal direction. Similarly, when the bristles are oriented distally, the guidewire may be moved freely in the distal direction but will be resistant to motion in the proximal direction. In each case, a larger force will be required to initiate motion of the guidewire in a direction opposite the orientation of the bristles than to initiate motion in the direction in which the bristles are oriented.

While the bristles shown in FIG. 11 are annular elements whose thickness tapers from the outer radius of the annulus to the inner radius, the brushes need not be tapered inward and may consist of a series of spaced annuli of uniform thickness. Moreover, the bristles need not be annular but may rather consist of a series of flexible elements extending inward from the interior surface of the tip.

Brush 244 and bristles 245 may be made of suitable materials including olefinics, polyurethanes, polyesters, styrenics, polyamides and combinations thereof. Most importantly, it is desirable that the bristles not be made of a material which will scratch, nick or otherwise mar guidewire element 226.

As in the previous embodiment, guidewire element 226 may consist isolely of a guidewire or may further comprise a protective guidewire sheath. Where the guidewire element has a protective sheath bonded or otherwise affixed to the guidewire and the sheath and guidewire slide in unison, the shim will simultaneously engage the guidewire and sheath.

Figure 13:
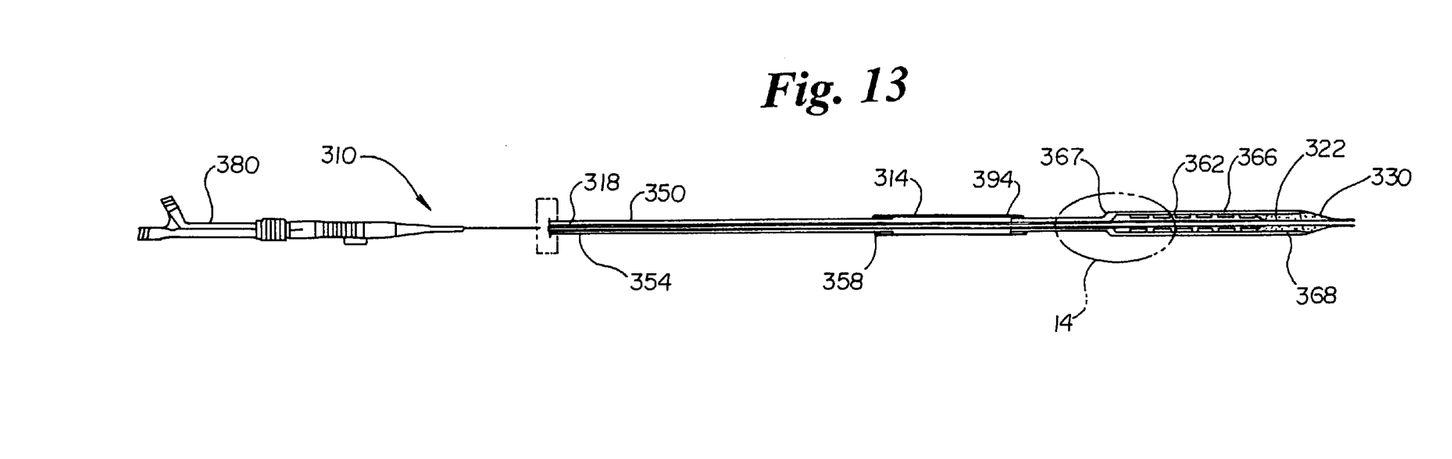
FIG. 13 shows another embodiment of the inventive catheter.

Another embodiment of the invention is shown in FIG. 13. A lockable treatment device delivery catheter, shown generally at 310, comprises an inner tube 314 having proximal 318 and distal 322 ends. Inner tube is carried in a catheter shaft 350 having proximal 354 and distal 358 ends, and extends beyond the distal end of the catheter shaft. The catheter further comprises a guidewire element (not shown) carried within inner tube 314 and extending from proximal end 318 of inner tube 314 to distal end 322 of inner tube 314. Mounted over inner tube 314 at distal end 322 of inner tube 314 is a tip 330. A retractable sheath 366 having proximal 367 and distal 368 ends is slidably mounted on distal catheter shaft 394 retracting from a fully extended position in which a treatment device 362 (shown here as a stent) is covered by the retractable sheath and a fully retracted position in which treatment device 362 is exposed. Retractable sheath 366 may be retracted by pulling on sheath pullwire 369 which is attached to pull collar 365 which, in turn, is attached to retractable sheath 366. Sheath pullwire 369 extends to the proximal end of the catheter. Tip 330 abuts retractable sheath 366 in the fully extended position.

Figure 14:
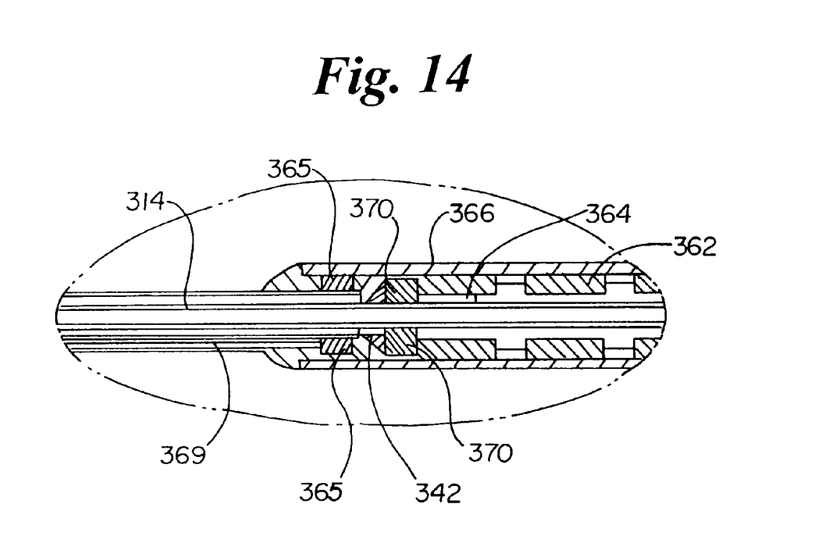
FIG. 14 shows an enlarged view of the circled region 14 of the catheter in FIG. 13.

Finally, catheter 310 comprises a motion arresting device comprising a locking cable 342 extending from proximal end 354 of catheter shaft 350 to proximal end 367 of retractable sheath 366. At least a portion of locking cable 342 is carried within catheter shaft 350. As shown in FIG. 14, locking cable 342 is anchored in retractable sheath 366, to bumper 370. For the sake of clarity it should be noted that pullwire 369 and locking cable 342 appear to merge into one in FIG. 14. This is an artifact of the figure. In reality, the two are separate and distinct.

Figure 15:
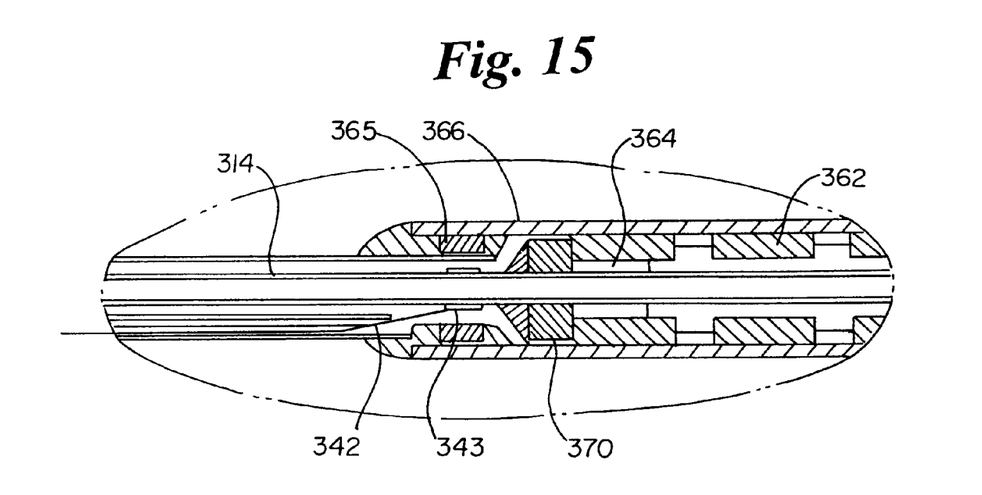
FIG. 15 shows an enlarged view of a portion of the distal end of another embodiment of the inventive catheter.

Locking cable 342 may be alternatively anchored to any other suitable structure in the distal end of the catheter. FIG. 15 shows another embodiment of the distal end of a catheter identical to that shown in FIGS. 13 and 14 with the exception that locking cable 342 is anchored to positioning collar 343. In either embodiment, prior to being engaged, locking cable 342 has some slack in it.

At the proximal end of the catheter is an optional manifold structure 380 with slide mechanism 382 as is known in the art. Slide mechanism 382 is connected to pullwire 369 in a known manner for retracting sheath 366 by moving the slide proximally. Also shown in FIGS. 14 and 15 are marker bands 364 as are known in the art.

In use, locking cable 342 may be engaged to prevent motion of tip 330 by placing the locking cable in tension or by placing the locking cable in compression thereby stiffening the catheter. Ideally, the application of the locking cable will occur as part of the final positioning of the catheter. The catheter may be unlocked by reducing the tension or compression of the cable.

While the locking cable may be made of any suitable material such as a metal, the material must be rigid enough so that it does not buckle when placed in compression if used as a compression cable. It is preferable that the locking cable be carried in a tube. Suitable materials for the locking cable include Nitinol and stainless steel.

The present invention is not intended to be limit to catheters as shown here in the figures. Other configurations of the catheter are also contemplated for use in conjunction with the present invention including catheters having full length sheaths such as in U.S. Pat. No. 4,875,480 to Imbert, catheters employing the collapsible sheath technique of U.S. Pat. No. 5,534,007 and PCT patent application PCT/US96/07143 and catheters having slidably sealed sheaths and midshaft seals as disclosed in U.S. patent application Ser. No. 08/722,834 filed Sep. 27, 1996, as well as U.S. patent application Ser. No. 09/071,484 filed May 1, 1998. The entire contents of the above-mentioned patents and patent applications are hereby incorporated in their entirety by reference herein.

Further, as shown above in the figures, the treatment device may be a stent. A variety of stents are suitable for use with the inventive catheters including self-expanding and balloon expandable stents. In the latter case, a balloon is mounted concentrically over the distal end of the inner tube and at least a portion of the stent mounted over the balloon and concentrically over the inner tube. In the case of the balloon expandable stent, the catheter will further comprise a suitable inflation shaft having a lumen therein for inflating the balloon. Such inflation shafts well known in the art.

Other treatment devices in addition to stents are contemplated including a balloon for angioplasty procedures and a laser for laser ablation procedures.

The present invention also provides a catheter of variable flexibility. The catheter comprises a catheter shaft having proximal and distal end, an inner tube having proximal and distal ends, extending from the proximal end of the catheter shaft and carried within the catheter shaft, a guidewire element carried within the inner tube and extending from the proximal end of the inner tube to the distal end of the inner tube and a tension-compression cable for altering the flexibility of the catheter, the tension-compression cable anchored to an anchoring element at the distal end of the catheter shaft, the tension-compression cable having a relaxed state in which no tension or compression is applied thereto. The catheter may be made more rigid by applying tension or compression to the cable in its relaxed state. Embodiments of the variably flexible catheter are shown in FIGS. 14 and 15.

Figure 16:
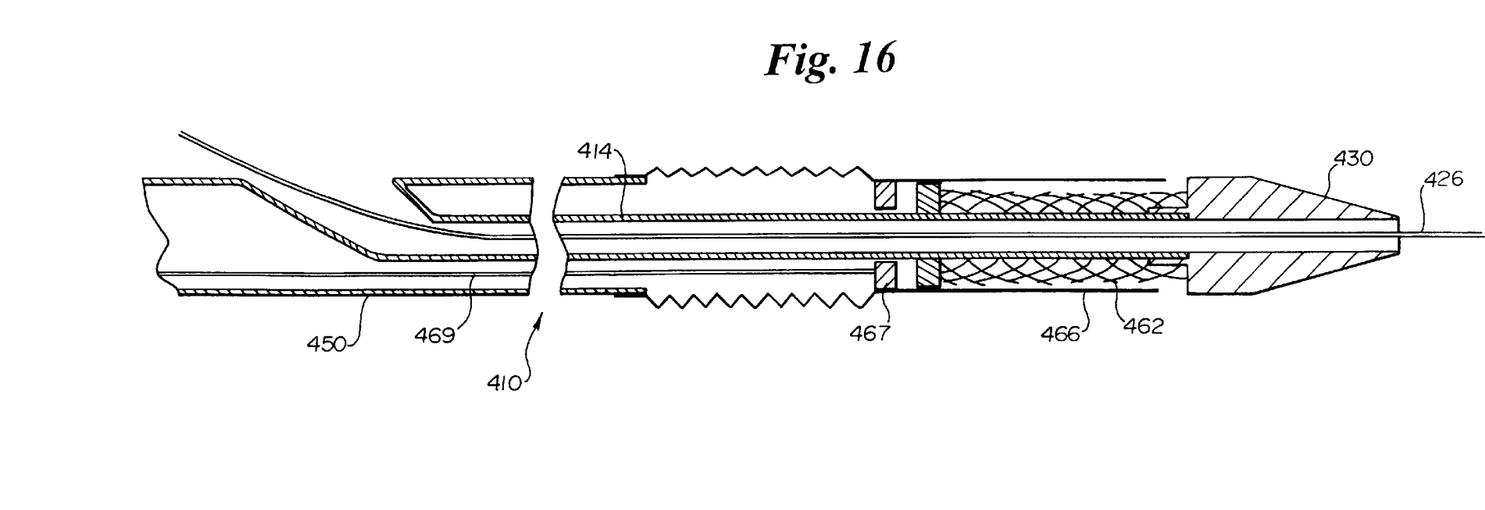
FIG. 16 shows a catheter in rapid exchange form.

The invention is also directed to a rapid exchange catheter with a motion arresting device. FIG. 16 shows a rapid exchange catheter generally at 410. Catheter 410 includes a cather shaft 450 having a guidewire lumen 414 extending at least a portion of the way through the distal end of catheter shaft 450. Guidewire lumen 414 terminates in a tip 430 located at its distal end. Tip 430 has an opening extending therethrough to accommodate a guidewire. Guidewire 426 enters catheter shaft 450 in guidewire lumen 414 and emerges through the opening in tip 430. The tip of catheter 410 may be suitably modified to incorporate any of the tip-based motion arresting devices disclosed herein including the shim and the annular brush.

Catheter 410 is shown with a stent 462 disposed about guidewire lumen 414. Stent 462 is covered by retractable sheath 466. Retractable sheath 466 is affixed to pull collar 467. Pull collar 467, in turn, has a pull wire 469 extending proximally therefrom for retracting the sheath.

The above Examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is as follows:

1. A lockable treatment device delivery catheter comprising:
    an inner tube having proximal and distal ends;
    a guidewire element carried within the inner tube and extending from the proximal end of the inner tube to the distal end of the inner tube;
    a tip disposed at the distal end of the inner tube; and
    a motion arresting device frictionally engaging the tip with the guidewire to prevent motion of the tip when engaged,
    the motion arresting device comprising an annular brush having bristles, the brush disposed within the tip about the guidewire element, the bristles extending from the brush to the guidewire element and frictionally engaging at least a portion of the guidewire element.

2. The lockable treatment device delivery catheter of claim 1 wherein the bristles are made of a soft material which does not mar the guidewire element.

3. The lockable treatment device delivery catheter of claim 1 further comprising:
    a catheter shaft having proximal and distal ends, the inner tube carried within the catheter shaft and extending beyond the distal end of the catheter shaft;
    a treatment device disposed about the distal end of the inner tube; and
    a retractable sheath slidably disposed about the distal end of the catheter shaft, the sheath retractable from a fully extended position in which the treatment device is covered by the retractable sheath and a fully retracted position in which the treatment device is exposed, the tip abutting the retractable sheath in the fully extended position.

4. The lockable treatment device delivery catheter of claim 3 wherein the treatment device is a stent disposed about the distal end of the inner tube, the stent covered when the retractable sheath is in the fully extended position, the stent fully exposed when the retractable sheath is in the retracted position.

5. The lockable treatment device delivery catheter of claim 4 wherein the stent is self-expanding.

6. The lockable treatment device delivery catheter of claim 1 further comprising:
    a balloon-expandable stent disposed about the inner tube,
    a fluid inflatable balloon disposed about the inner tube underneath the stent,
    and an inflation lumen in fluid communication with the balloon and extending to the proximal end of the catheter shaft.

7. The lockable treatment device delivery catheter of claim 1 in rapid exchange form.

8. The lockable treatment device delivery catheter of claim 1 in over-the-wire form.

9. A method of delivering a treatment device to a desired bodily location comprising the steps of:
    providing the lockable treatment device delivery catheter of claim 1 having a treatment device disposed about the inner tube, the motion arresting device comprising an annular brush having bristles, the brush disposed within the tip about the guidewire element, the bristles extending from the brush to the guidewire element and frictionally engaging at least a portion of the guidewire element:

inserting the lockable treatment device delivery catheter into a bodily vessel;

delivering the treatment device to the desired bodily location;

locking the tip in place by engaging the motion arresting device;

retracting the retractable sheath;

deploying the treatment device; and removing the lockable treatment device delivery catheter from the bodily vessel.

10. A lockable stent delivery catheter comprising:

an inner tube having proximal and distal ends;

a catheter shaft having proximal and distal ends, the inner tube carried within the catheter shaft and extending beyond the distal end of the catheter shaft;

a guidewire element carried within the inner tube and extending from the proximal end of the inner tube to the distal end of the inner tube;

a retractable sheath slidably disposed about the distal end of the inner tube, the retractable sheath retractable from a fully extended position to a fully retracted position;

a tip disposed at the distal end of the inner tube, the tip abutting the retractable sheath in the fully extended position, the tip having a proximal region character by an inner diameter and a intermediate region distal to and adjacent to the proximal region, the intermediate region having an inner diameter exceeding the inner diameter of the proximal region of the tip;

a motion arresting device frictionally engaging the tip with the guidewire to prevent motion of the tip when engaged, the motion arresting device comprising an annular brush having bristles, the brush disposed within the intermediate region of the tip about the guidewire element, the bristles extending from the brush to the guidewire element and frictionally engaging at least a portion of the guidewire element; and a stent disposed about the distal end of the inner tube, the stent covered by the retractable sheath when the retractable sheath is in the fully extended position, the stent exposed when the retractable sheath is in the fully retracted position.

11. The lockable treatment device delivery catheter of claim 10 wherein the stent is self-expanding.

12. The lockable treatment device delivery catheter of claim 10 wherein the stent is balloon-expandable, the catheter further comprising a fluid expandable balloon disposed about the distal end of the inner tube underneath the stent, and an inflation lumen in fluid communication with the balloon and extending to the proximal end of the catheter shaft.

* * * * *

UNITED STATES PATENT AND TRADEMARK OFFICE
CERTIFICATE OF CORRECTION

PATENT NO.   : 6,228,110 B1
DATED        : May 8, 2001
INVENTOR(S)  : Joel R. Munsinger It is certified that error appears in the above-identified patent and that said Letters Patent is hereby corrected as shown below:

<u>Column 6,</u>
Line 6, delete "isolely" and insert -- solely. --

<u>Column 9,</u>
Line 25, delete "character" and insert -- characterized. --

Signed and Sealed this

Thirteenth Day of November, 2001

*Attest:*

NICHOLAS P. GODICI
*Attesting Officer*   *Acting Director of the United States Patent and Trademark Office*